(12) United States Patent
Balaban et al.

(10) Patent No.: US 7,109,872 B2
(45) Date of Patent: Sep. 19, 2006

(54) APPARATUS AND METHOD FOR POSTURAL ASSESSMENT WHILE PERFORMING COGNITIVE TASKS

(75) Inventors: Carey David Balaban, Pittsburgh, PA (US); Mark Steven Redfern, Pittsburgh, PA (US)

(73) Assignee: University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 90 days.

(21) Appl. No.: 10/840,791

(22) Filed: May 6, 2004

(65) Prior Publication Data

US 2004/0222892 A1 Nov. 11, 2004

Related U.S. Application Data

(60) Provisional application No. 60/468,327, filed on May 6, 2003.

(51) Int. Cl.
G08B 23/00 (2006.01)
(52) U.S. Cl. .................. 340/573.7; 340/575; 340/576; 340/573.1; 600/300
(58) Field of Classification Search ............. 340/573.7, 340/573.1, 575, 576, 439, 665, 666, 667; 600/300
See application file for complete search history.

(56) References Cited

U.S. PATENT DOCUMENTS

| | | | |
|---|---|---|---|
| 4,622,644 A | 11/1986 | Hansen | |
| 4,642,786 A | 2/1987 | Hansen | |
| 4,710,708 A | 12/1987 | Rorden et al. | |
| 4,849,692 A | 7/1989 | Blood | |
| 4,945,305 A | 7/1990 | Blood | |
| 5,142,506 A | 8/1992 | Edwards | |
| 5,450,752 A | 9/1995 | White et al. | |
| 5,465,079 A * | 11/1995 | Bouchard et al. | 340/576 |
| 5,591,914 A | 1/1997 | White et al. | |
| 5,600,330 A | 2/1997 | Blood | |
| 5,680,041 A | 10/1997 | Begin | |
| 5,744,953 A | 4/1998 | Hansen | |
| 5,767,669 A | 6/1998 | Hansen et al. | |
| 5,804,961 A | 9/1998 | Castillo et al. | |
| 5,821,743 A | 10/1998 | Page, Jr. et al. | |
| 5,831,260 A | 11/1998 | Hansen | |
| 5,953,683 A | 9/1999 | Hansen et al. | |
| 5,998,991 A | 12/1999 | Begin | |
| 6,124,708 A | 9/2000 | Dames | |
| 6,158,768 A * | 12/2000 | Steffens et al. | 280/735 |
| 6,172,499 B1 | 1/2001 | Ashe | |
| 6,246,231 B1 | 6/2001 | Ashe | |
| 6,324,453 B1 * | 11/2001 | Breed et al. | 701/45 |
| 6,392,550 B1 * | 5/2002 | Najor | 340/576 |
| 6,404,183 B1 | 6/2002 | Piana | |
| 6,528,991 B1 | 3/2003 | Ashe | |
| 6,539,327 B1 | 3/2003 | Dassot et al. | |

OTHER PUBLICATIONS

G. Andersson et al., "A Dual-task Study of Interference Between Mental Activity and Control of Balance", The American Journal of Otology, 1998, pp. 632-637.

(Continued)

*Primary Examiner*—Anh V. La
(74) *Attorney, Agent, or Firm*—Arnold B. Silverman; Robert A. Diaz; Eckert Seamans Cherin & Mellott, LLC

(57) ABSTRACT

A postural assessment chair provides a device for monitoring the posture of an individual seated thereon, and correlating changes in the individual's posture, along with indicia of movement of the chair itself and the cognitive workload of the individual, to determine the mental engagement of the individual.

11 Claims, 16 Drawing Sheets

OTHER PUBLICATIONS

R. L. Burden et al., "Numerical Analysis" Youngstown State University, pp. 146-163 and 426-449, Fourth Edition, PWS-KENT Publishing Company, Boston.

Logitech, "3D Mouse & Head Tracker" Technical Reference Manual, 87 pgs.

* cited by examiner

High Cognitive Workload
- Strong Bacing Posture
- 'Edge of Seat' Posture
- Tightly Constrained Body Linkages.

APPARATUS AND METHOD FOR POSTURAL ASSESSMENT WHILE PERFORMING COGNITIVE TASKS

CROSS REFERENCE TO RELATED APPLICATION

This Application claims the benefit of U.S. Provisional Patent Application Ser. No. 60/468,327, filed May 6, 2003.

GOVERNMENT LICENSE RIGHTS

The U.S. Government has a paid-up license in this invention and the right in limited circumstances to require the patent owner to license others on reasonable terms as provided for by the terms of Grant No. N00014-02-0808 of the Office of Naval Research.

BACKGROUND OF THE INVENTION

1. Field of the Invention

The present invention relates to an apparatus and method for analyzing postural changes to assess mental engagement during cognitive tasks.

2. Description of the Related Art

Determining the degree of mental engagement in cognitive work is potentially critical for a wide range of tasks, including flying an airplane, operating a boat, air traffic control, operation of automobiles, and/or operation of unmanned robotic vehicles through virtual interfaces.

Present efforts towards analyzing cognitive engagement focus on identifying physiological measures from neural or physiological domains and attempting to correlate these measures to cognitive states. For example, EEG or pupillometry are highly susceptible to eye movement, blinking, and other sources of activity, in addition to the time between EEG recording and food intake. Accordingly, there is a need for an apparatus and method for measuring automatic motor behaviors to measure cognitive engagement.

Presently available means of measuring the position and orientation of sensors attached to various body parts, such as the head, arms, legs or torso, include magnetic positioning sensors such as those marketed by Ascension Technology Corp. under the trademark FLOCK OF BIRDS. The operation of such motion tracker is explained in U.S. Pat. Nos. 5,744,953 and 5,831,260. The algorithms for determining the position and orientation of the sensors with respect to a reference sensor are best explained in U.S. Pat. Nos. 4,849,692, 4,945,305, and 6,172,499.

Presently available position and orientation measuring means using ultrasonic positional sensors include those marketed by Logitech, Inc., and are described in U.S. Pat. No. 5,142,506. Other ultrasonic position measuring devices are disclosed in U.S. Pat. Nos. 5,450,752 and 5,591,914.

Although there are presently available means for monitoring the position and orientation of various body parts, there is a need for correlating these measurements with cognitive engagement so that they may be used as a measure of cognitive engagement during the performance of cognitive work. Additionally, there is a need to perform these measurements upon seated personnel during the performance of cognitive tasks.

SUMMARY OF THE INVENTION

The above-described needs and others are met by the present invention, which provides an apparatus and method for dynamic postural assessment of seated personnel.

The present invention provides a chair equipped with a plurality of sensors for determining changes in posture. For example, these sensors may include pressure sensors within the seat and back pad of the chair. Additionally, these sensors may include magnetic positioning sensors on the chair itself and worn by person seated on the chair, for example, on the head or torso. These positioning sensors may be, for example, magnetic or ultrasound positioning sensors. Additional sensors including motion sensors, possibly having accelerometers and/or rate sensors therein, may be mounted within the seat itself to monitor movement of the vehicle within which the seat is mounted. Lastly, the apparatus includes a computer for monitoring the signals collected by the sensors and the workload of the person seated in the chair, and to perform the postural assessment.

The method of postural assessment begins by recording the initial readings of the various pressure and/or position sensors. As the seated person performs cognitive tasks, the position of the head and/or torso, the position of the seat, and/or the pressure exerted on the seat and back pad, may all be measured. These measurements may then be compared with the workload of the individual at that point in time, along with the movement of any vehicle within which the individual may be seated, and analyzed to determine the level of cognitive engagement of the individual. An example of postural indicators of cognitive engagement include movement of the head towards a visual display corresponding to an increasing number of tasks presented by the visual display. Alternatively, an individual may leave his head relatively close to the visual display to maintain vigilance as the workload presented by the visual display decreases, until the individual is satisfied that the level of work is tapering off. The individual may also alter his posture in response to movements of the vehicle within which the chair is located, for example, compensating for the rhythmic movements of a boat or the angle of flight of an airplane or helicopter. Furthermore, the pressure exerted by the individual upon the chair will indicate the level of cognitive engagement, with a large pressure concentrated over a small area indicating a braced posture and high level of mental engagement, and a lower pressure distributed over a larger area being indicative of a relaxed posture and lowered cognitive engagement. A high standard deviation of the rate of change in pressure between various sensors at a given point in time is indicative of changes in posture that may indicate fidgeting (impatience), fatigue and a need to relieve personnel. As another alternative, the center of pressure applied by the right and left buttock may be determined, and the movements of these centers of pressure may be analyzed in the same manner as head movement, with forward movement of the centers of pressure indicating torso and head movement towards a visual display of a workload. Again, changes in pressure from one side to the other that deviate from the known patterns of the individual, or the movement characteristics of the vehicle in which the person is sitting, may indicate fatigue.

The present invention is therefore useful for a wide variety of individuals who perform tasks for which monitoring cognitive engagement is important. Examples include pilots, those working aboard a ship, vehicle drivers, air traffic controllers, and others who perform their work while seated. Upon detection of posture changes indicative of fatigue, additional stimulus may be provided to increase cognitive engagement, or personnel may be relieved if performance degrades below acceptable levels. Additionally, the present invention provides a means of assessing the balance function in medical patients who are incapable of standing for prolonged periods of testing.

It is therefore an object of the present invention to provide an apparatus for dynamic postural assessment of seated individuals during performance of cognitive tasks.

It is another object of the present invention to provide a method of measuring mental engagement of seated individuals during the performance of cognitive tasks.

It is a further object of the present invention to provide a means of dynamic measurement of postural changes of seated individuals, and correlating these postural changes with various levels of cognitive engagement.

It is another object of the present invention to provide a means for assessing the balance function in medical patients who are incapable of standing for prolonged periods of time.

It is a further object of the present invention to provide a determination of when to provide additional stimulus to personnel performing seated cognitive work in order to increase mental engagement.

It is another object of the present invention to provide a means for determining when seated personnel performing cognitive work need to be relieved due to fatigue or impatience.

These and other objects of the invention will become more apparent through the following description and drawings.

BRIEF DESCRIPTION OF THE DRAWINGS

Like reference characters denote like elements throughout the drawings.

DESCRIPTION OF THE PREFERRED EMBODIMENTS

The present invention provides an apparatus and method for measuring postural changes of a seated individual during the performance of cognitive tasks, and correlating these postural changes with the individual's level of mental engagement with the tasks.

Figure 1:
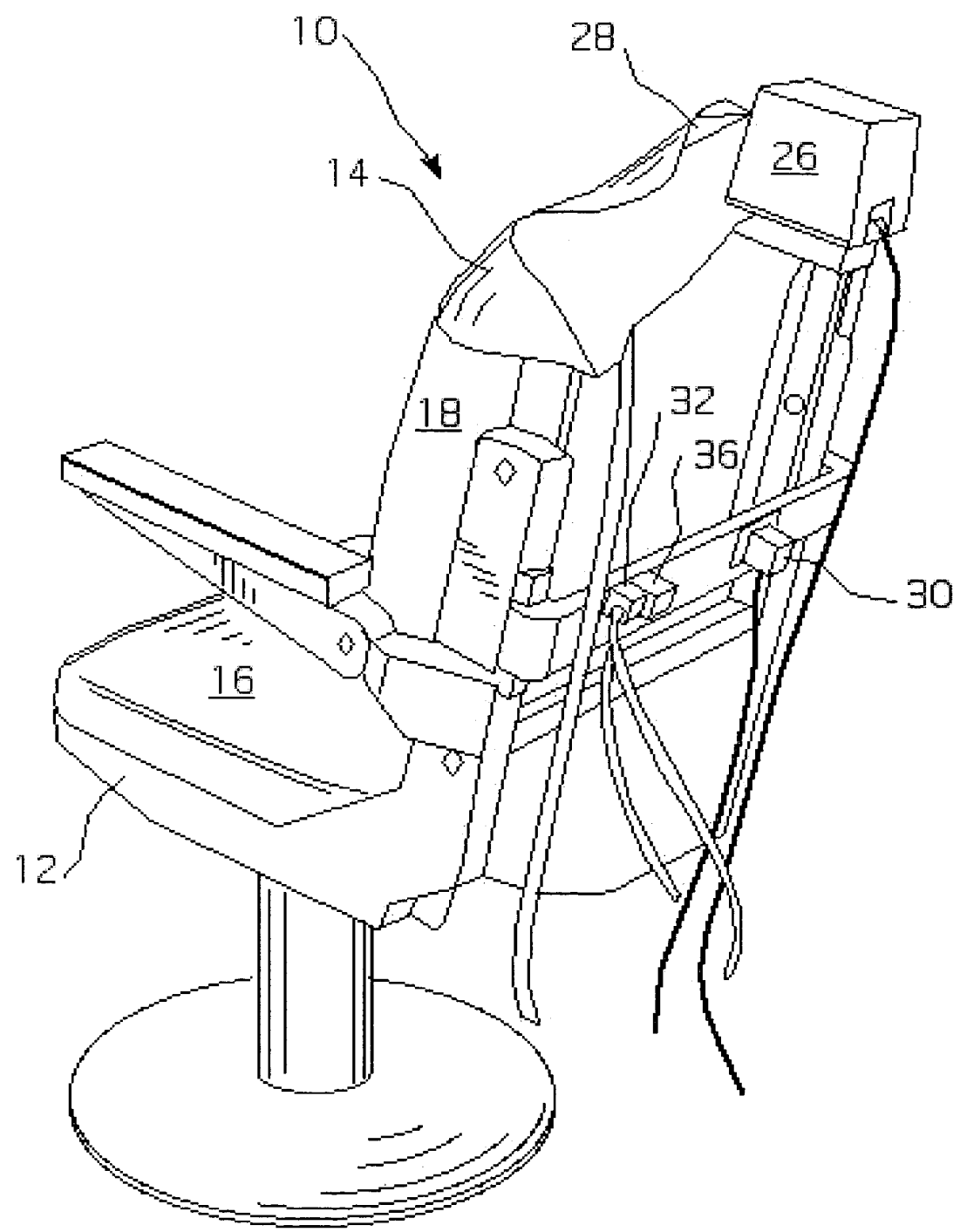
FIG. 1 is a back view photograph of a postural assessment chair according to the present invention.
Figure 2:
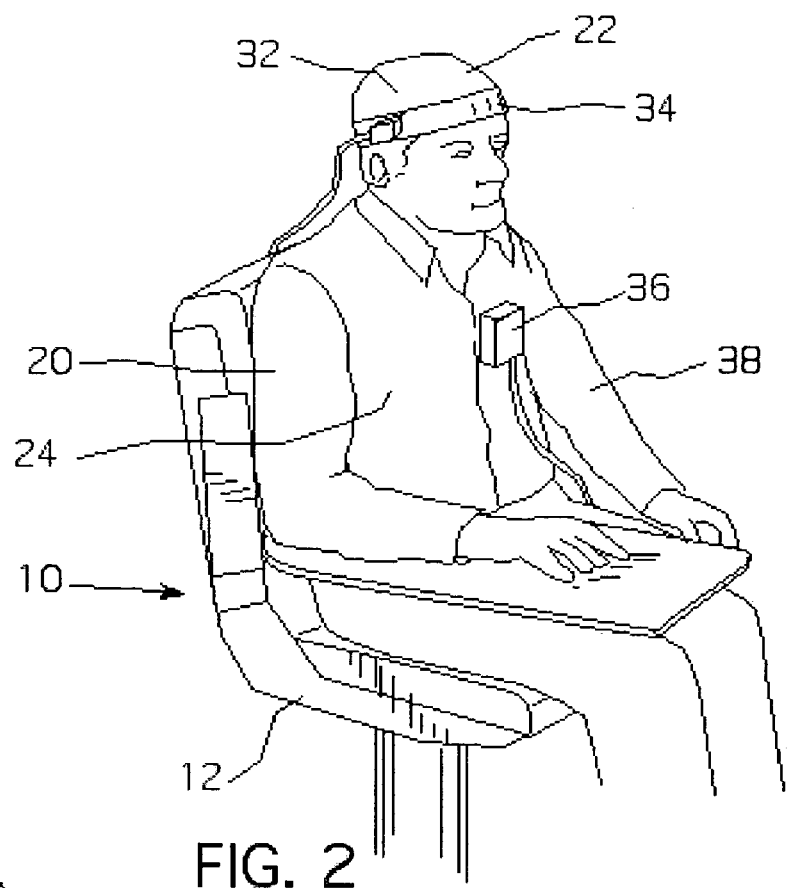
FIG. 2 is a photograph of an individual seated within a postural assessment chair according to the present invention.
Figure 3:
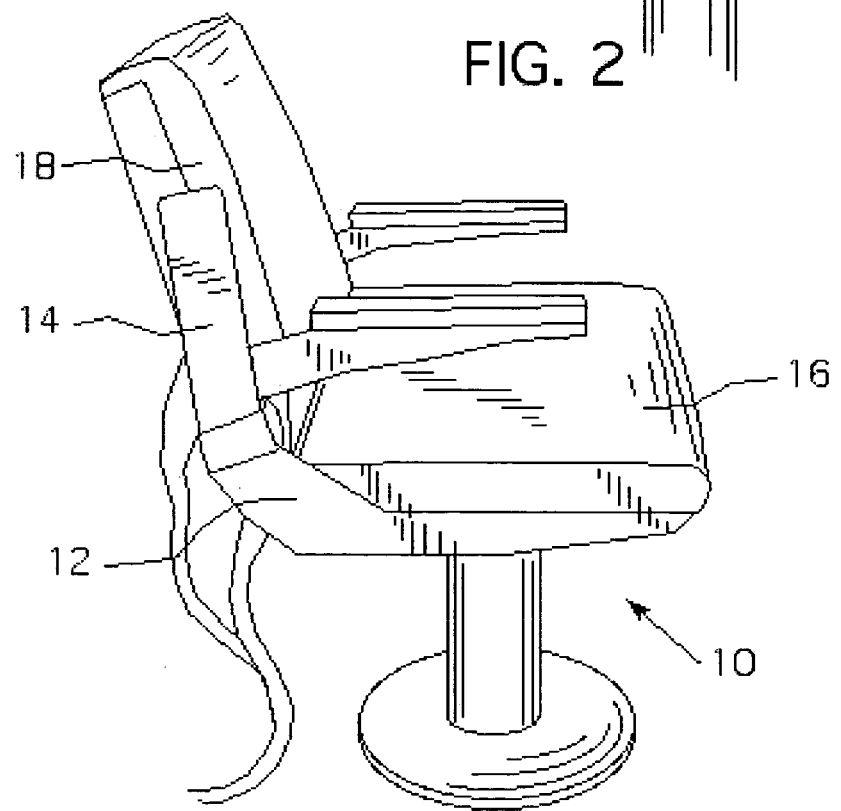
FIG. 3 is a side photograph of a postural assessment chair according to the present invention.

Referring to FIGS. 1–3, a postural assessment chair 10 is illustrated. The chair 10 includes a seat 12 and a back 14 each of which includes a pad 16, 18 having a plurality of pressure sensors therein. One preferred pressure sensitive pad is the FSA pad manufactured by Vista Medical. These pads 16, 18 each contain 256 sensors in a 16 by 16 pressure sensor array. These sensors typically operate at a rate of 4.5 Hz.

The chair 10 also may includes means for measuring the position and orientation of various body parts of the individual 20 seated within the chair 10, for example, the person's head 22, and/or chest 24. For this purpose, sensors marketed by Ascension Technology Corp. under the trademark FLOCK OF BIRDS may be used. A transmitter 26 is mounted on the chair 10, with a preferred location being near the top 28 of the back 14. A reference sensor 30 is mounted on the back 14. A head sensor 32 is worn by the person 20 sitting in the chair, possibly on headband 34, or alternatively within any helmet that may be worn by the individual performing the task for which measurement is desired. A chest sensor 36 is also worn by the person 20, possibly by being clipped to the person's shirt 38, or alternatively installed within a shoulder harness of a seat belt, if one is typically worn by the individual during performance of the task. Lastly, a 6 degree-of-freedom movement sensor having linear and angular accelerometers is mounted to the seat 12 of the chair 10. The operation of the transmitter 26, reference sensor 30, head sensor 32, and chest sensor 36 is well known to those skilled in the art of magnetic positioning and orientation sensors. Example methods of operation are described in U.S. Pat. Nos. 5,744,953 and 5,831,260, expressly incorporated herein by reference. Movement of the head sensor 32 and chest sensor 36 with respect to the reference sensor 30, may be detected as a combination of any of six different movements: forward and backward translation, side to side translation, upward and downward translation, rotation about a forward-backward axis, rotation about a side to side axis, and rotation about a vertical axis. The movement of each sensor may be calculated according to the signal received by the algorithms described in U.S. Pat. Nos. 4,849,692, 4,945,305, or 6,172,499, all of which are also expressly incorporated herein by reference.

Figure 18:
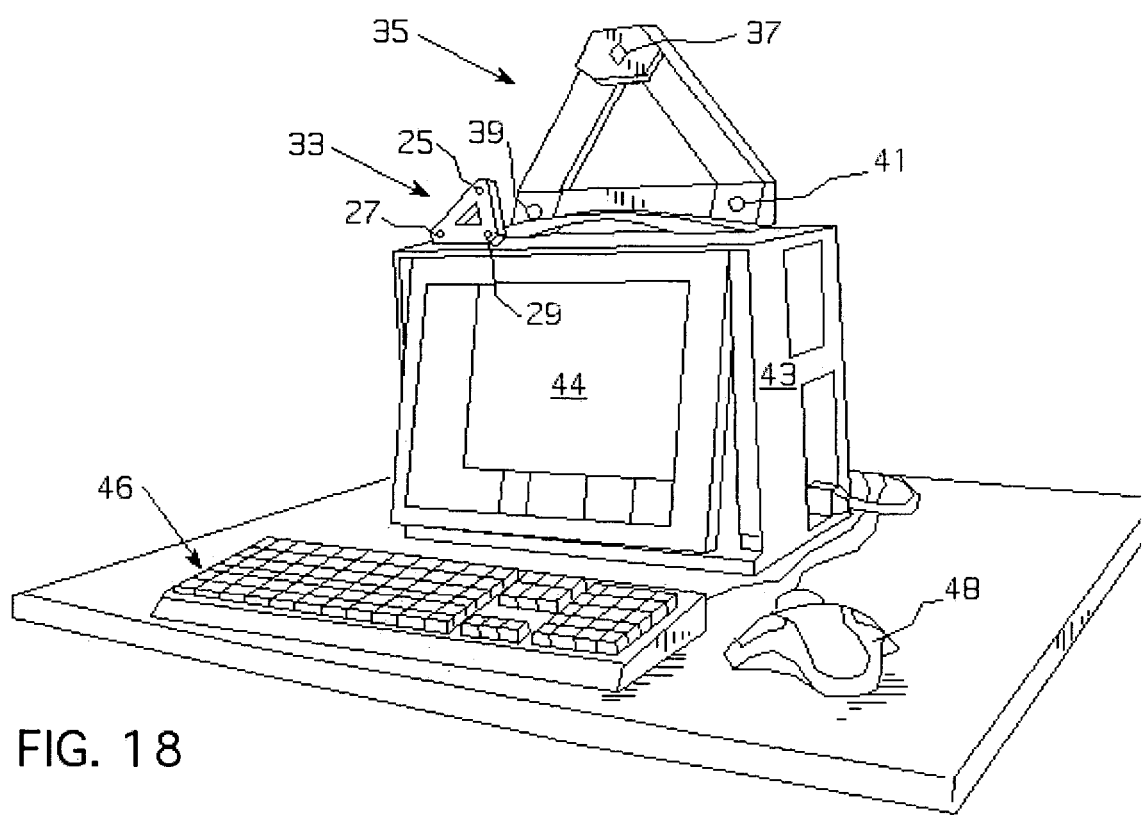
FIG. 18 is a front view of an ultrasonic position measurement system for use with a postural assessment system of the present invention.

Alternatively, an ultrasonic position sensor may be used. A preferred ultrasonic head tracker will have six degrees of freedom (both translation along and rotation around the x, y, and z axes) and may in some embodiments have a sampling rate of about 50 Hz. Such a sensor is presently offered by Logitech, Inc. of Fremont, Calif., on an exclusive marketing arrangement with VR Depot (www.vrdepot.com), and is disclosed in U.S. Pat. No. 5,142,506, which is expressly incorporated by reference. Referring to FIG. 18, a receiver 33, having one of the three microphones 25,27,29 at each apex of the triangle, may be worn on the head using a headband or any helmet typically worn while performing the task, and/or secured to the chest using a clip or any seatbelt typically worn during the task. An ultrasonic transmitter array 35, having one of the three speakers 37,39,41 at each apex of the triangle, may be mounted to a computer display or other fixed object in the workspace. The time required for the signal to travel from each speaker 37,39,41 to each microphone 25,27,29 can be used to calculate the position and orientation of the head and/or torso using well-known trigonometric principles.

Figure 6A:
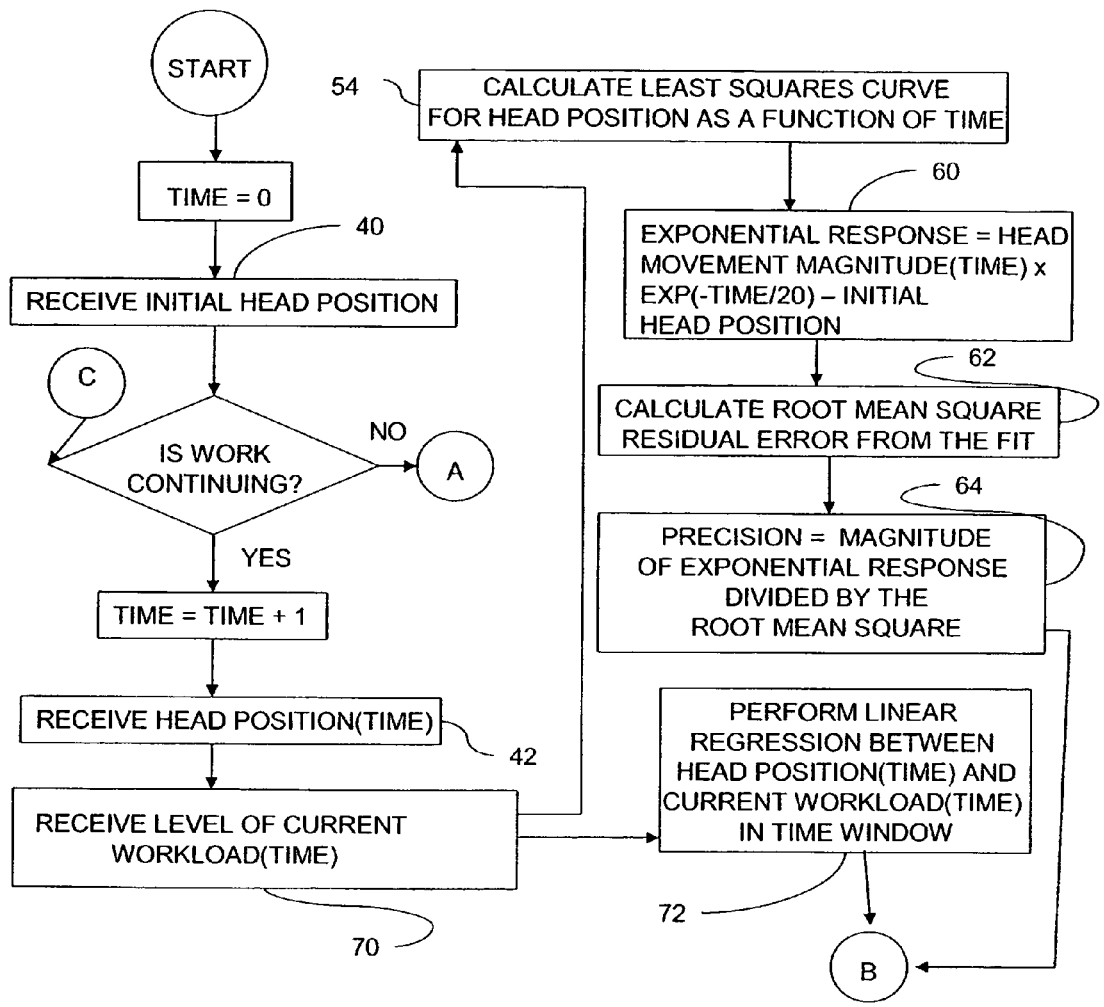
FIGS. 6A–6B are a flow chart illustrating the analysis of head movement for determining mental engagement.
Figure 6B:
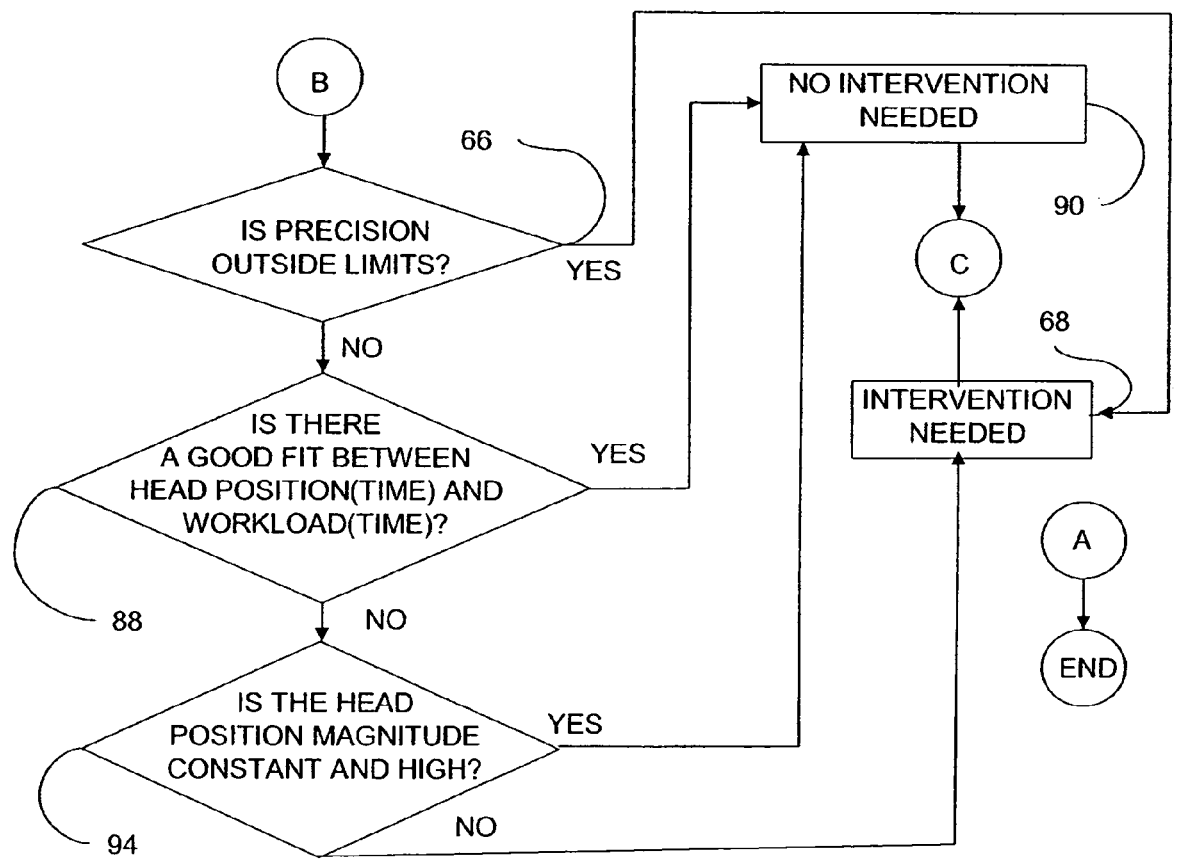
Figure 7:
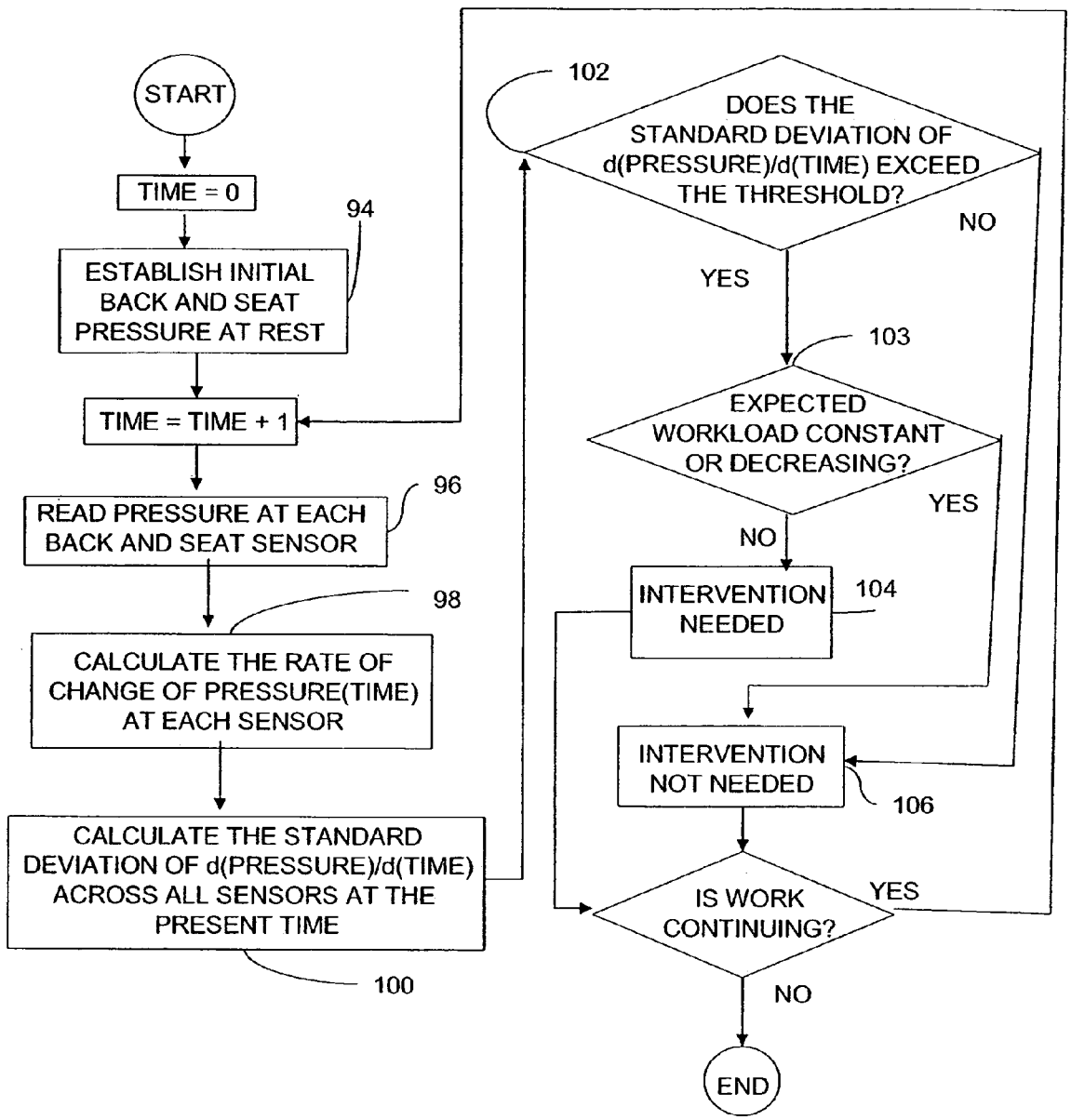
FIG. 7 is a flow chart illustrating the analysis of changes in seat pressure to determine cognitive engagement.
Figure 8:
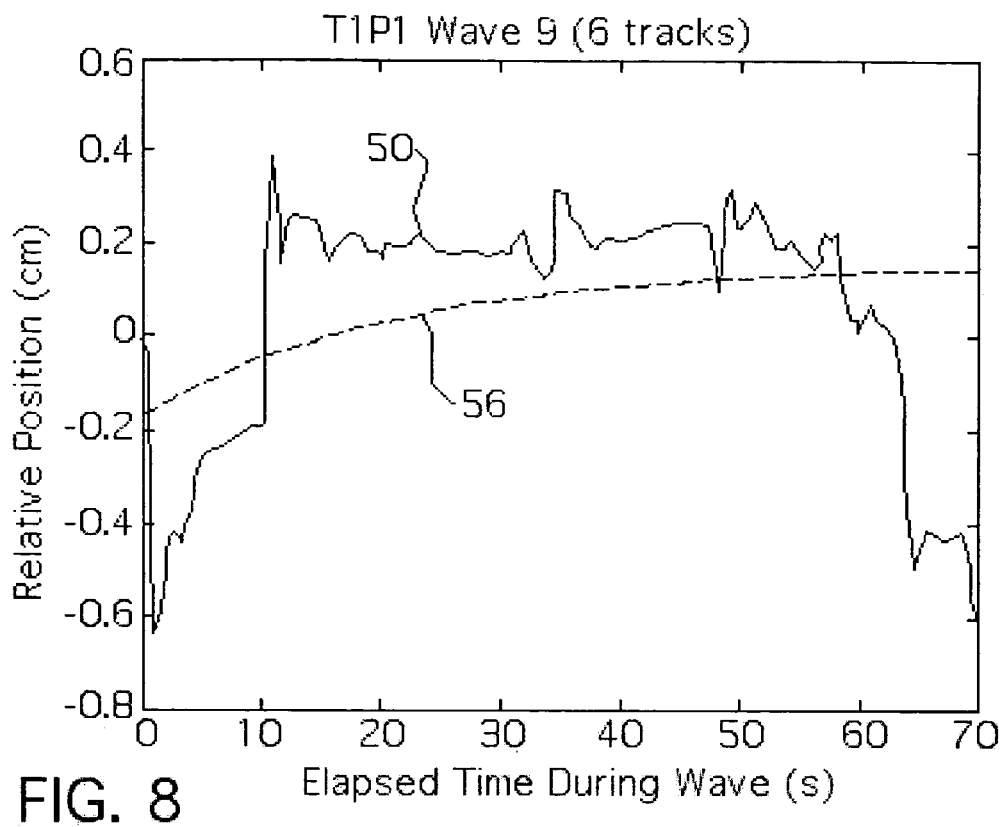
FIG. 8 is a graph illustrating head position as a function of time.
Figure 9:
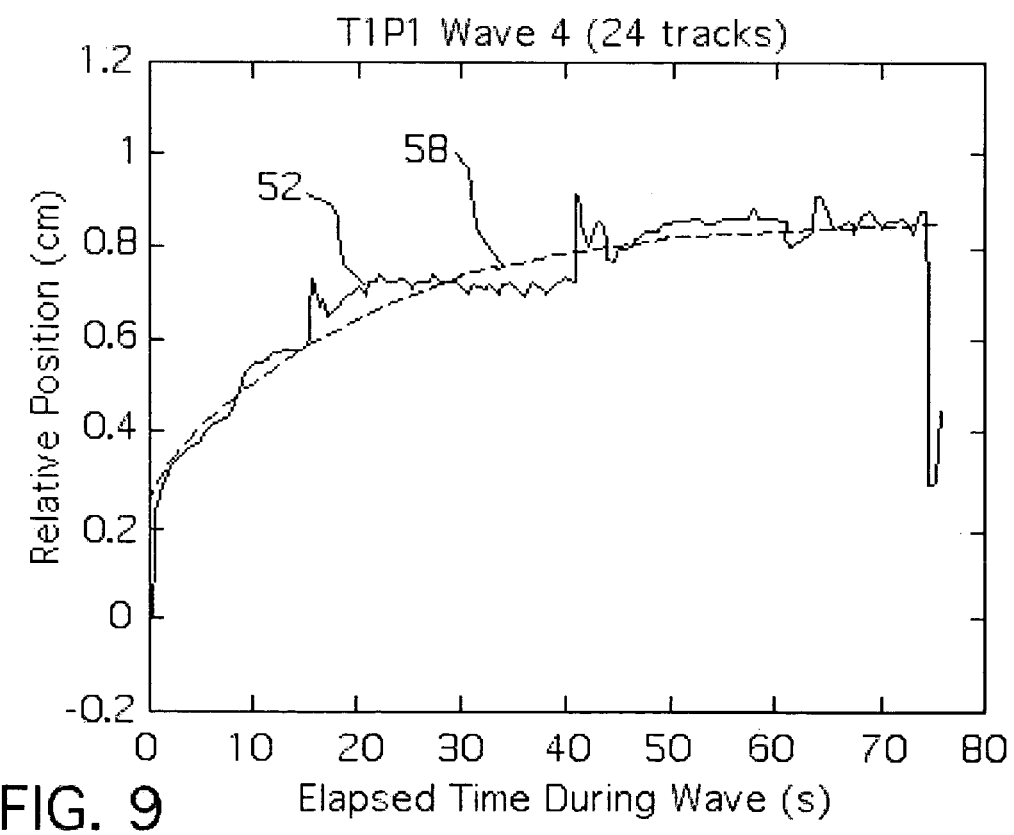
FIG. 9 is a graph illustrating head position as a function of time.

FIGS. 6–7 explain the basic method of using the chair 10 to monitor the posture of the person 20, and thereby monitor his level of mental engagement. Referring to FIGS. 6A–6B, the operation of the head sensor and its correlation to cognitive engagement are illustrated. Initially, the starting head position is received and recorded at 40. At each time increment, the head position at that time is recorded at 42. Referring briefly to FIGS. 8 and 9, an expected head position for various tasks is illustrated. Typically, the head will move from its rest position towards a visual stimulus, represented here by the computer monitor 44 (FIG. 1), or the implements used to perform the work, represented here by the keyboard 46 and mouse 48. FIGS. 8 and 9 were generated during an exercise wherein a person 20 played a video game simulating a warship commander task (Warship Commander, Pacific Science and Engineering, San Diego, Calif.). The task included monitoring planes displayed on the monitor 44, and using the mouse 48 to interrogate each plane to determine if it was a friend or foe, warn each foe that crossed a defensive perimeter, also using the mouse, and lastly using the mouse to shoot down any planes identified as a foe and remaining within the defensive perimeter three seconds after the warning. FIG. 8 represents a task involving six planes, and FIG. 9 represents a task involving 24 planes. The actual head movement is illustrated by the curves 50, 52, respectively. Typically, the head 22 will move towards the monitor 44 more rapidly at first, and then less rapidly, until a comfortable head position is reached for either performing the tasks or maintaining vigilance. This head movement can be represented by fitting the actual head movement points to a curve using least squares methodology, described in Richard L. Burden and J. Douglas Faires *Numerical Analysis, Fourth Edition*, 427–49 (1989), expressly incorporated herein by reference. This step is performed at step 54 in FIG. 6A, by the computer 43 (FIGS. 1 and 18) with the resulting curves illustrated as 56 in FIG. 8 and 58 in FIG. 9.

Figure 10:
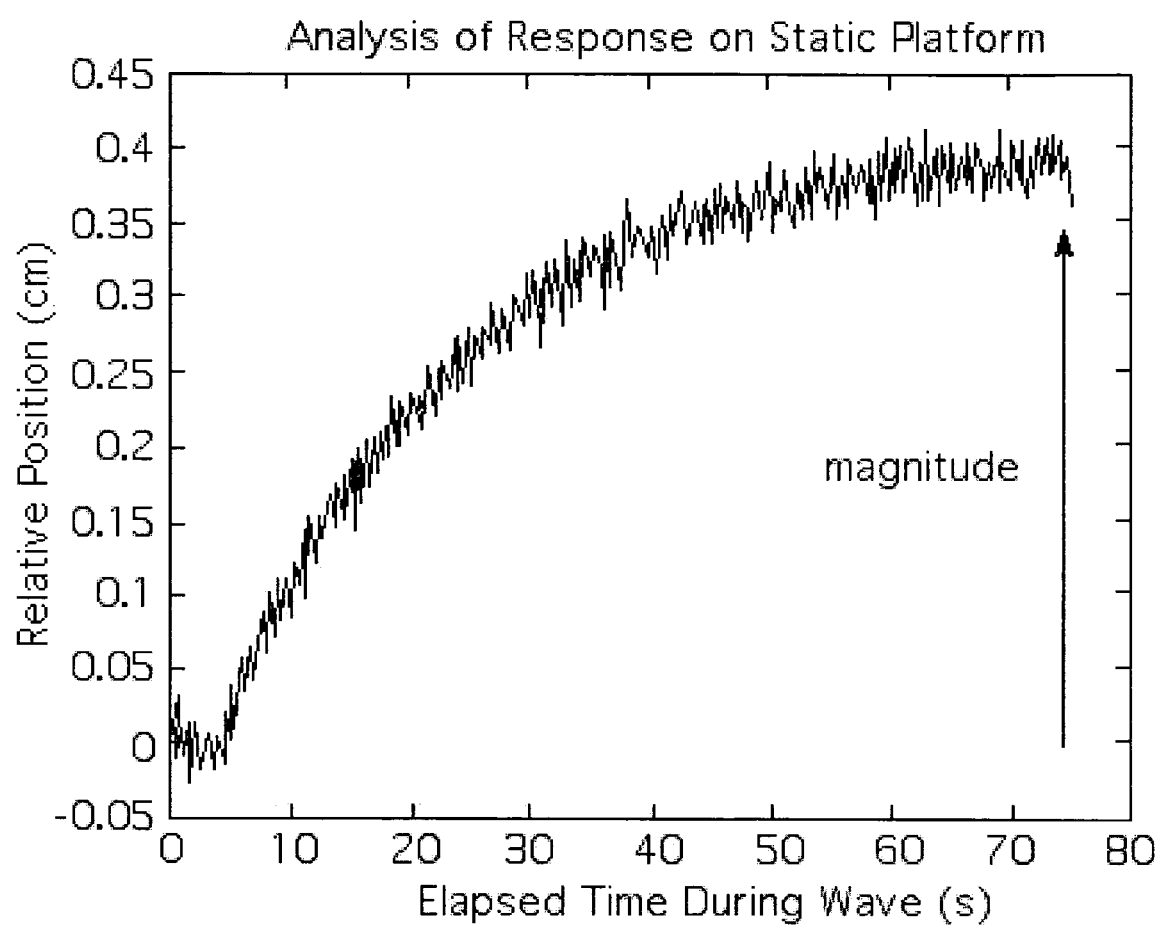
FIG. 10 is a graph illustrating the exponential response of head position with respect to time.
Figure 11:
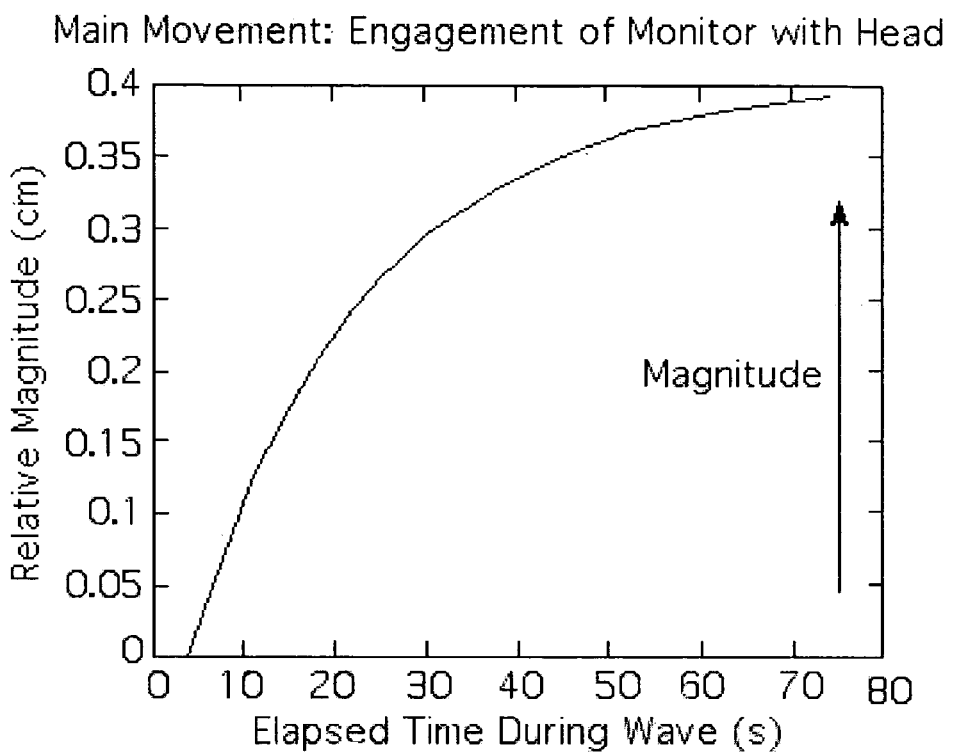
FIG. 11 is a graph illustrating the fitted curve for the exponential response of FIG. 10.
Figure 12:
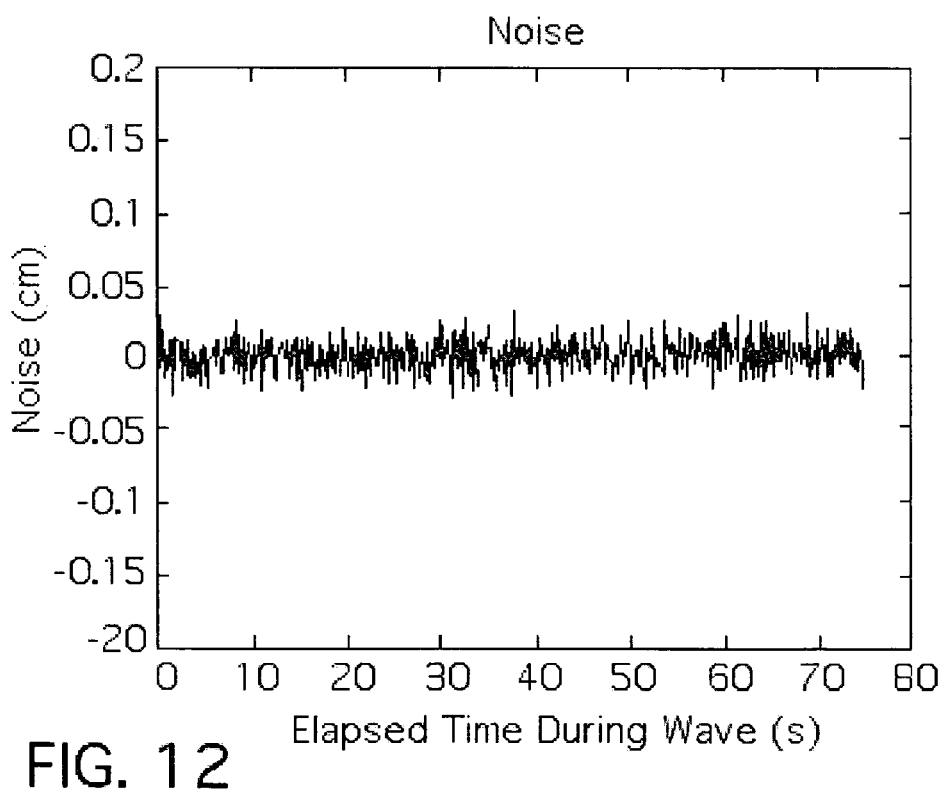
FIG. 12 is a graph illustrating the error of the exponential response of FIG. 10.

The head movement may be further analyzed by looking at an exponential response to the head movement with respect to time, with exponential response=((head movement magnitude) X exp(−time/20))−(initial head position). This calculation is performed at step 60 within FIG. 6A, with the resulting curve illustrated in FIG. 10. This curve may be further broken down into two separate elements: the curve itself as represented in FIG. 11, and the error between the actual data point and the approximated curve as shown in FIG. 12. By calculating the amount of the error, or the root means square of the exponential response, at step 62 in FIG. 6A, and then dividing the magnitude by the root means square at step 64, the possible degree of error in the head movement is shown. If this error is too high as determined at step 66 in FIG. 6B, this may be an indication that either additional stimulus or relief may be needed for the person 20, as provided at step 68 in FIG. 6B.

Figure 13A:
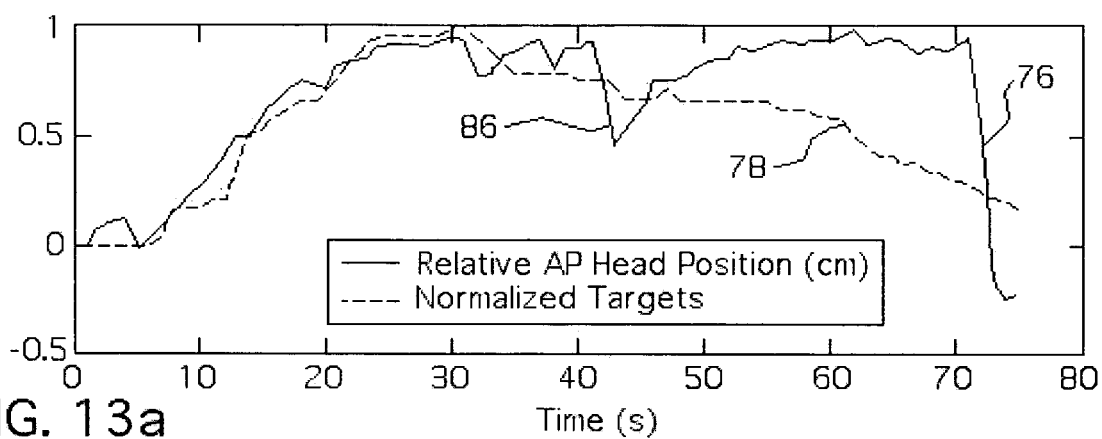
FIGS. 13a–b are graphs comparing head position to the workload with respect to time.
Figure 13B:
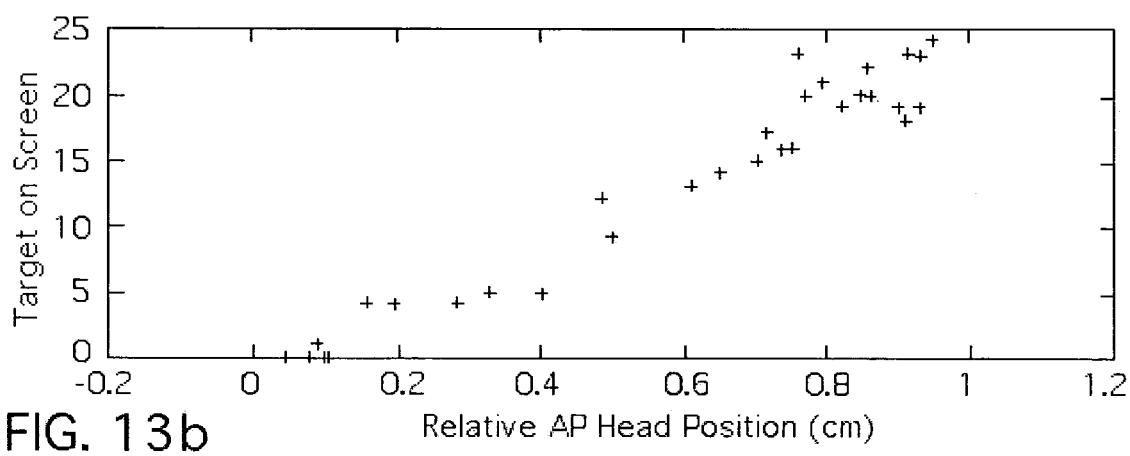
Figure 14A:
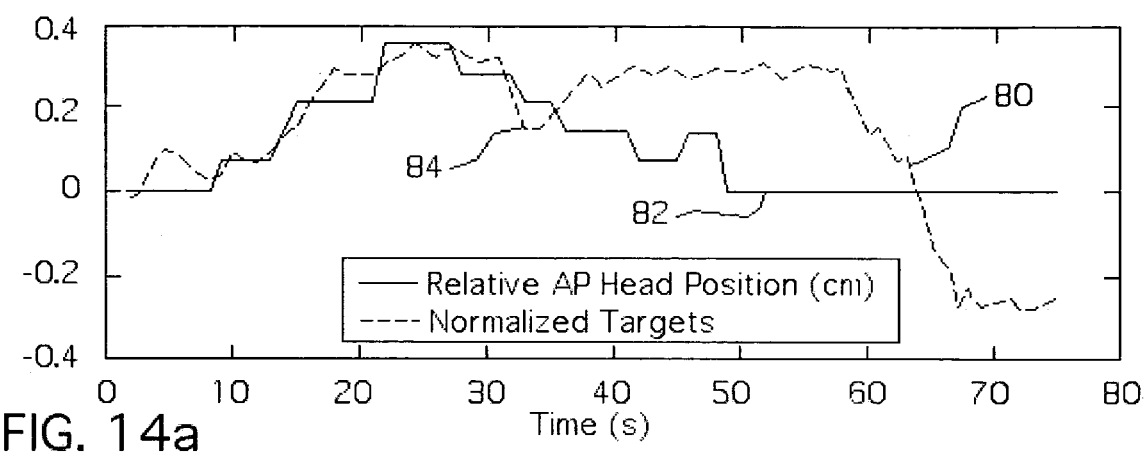
FIGS. 14a–14b are graphs illustrating head position and remaining workload with respect to time.
Figure 14B:
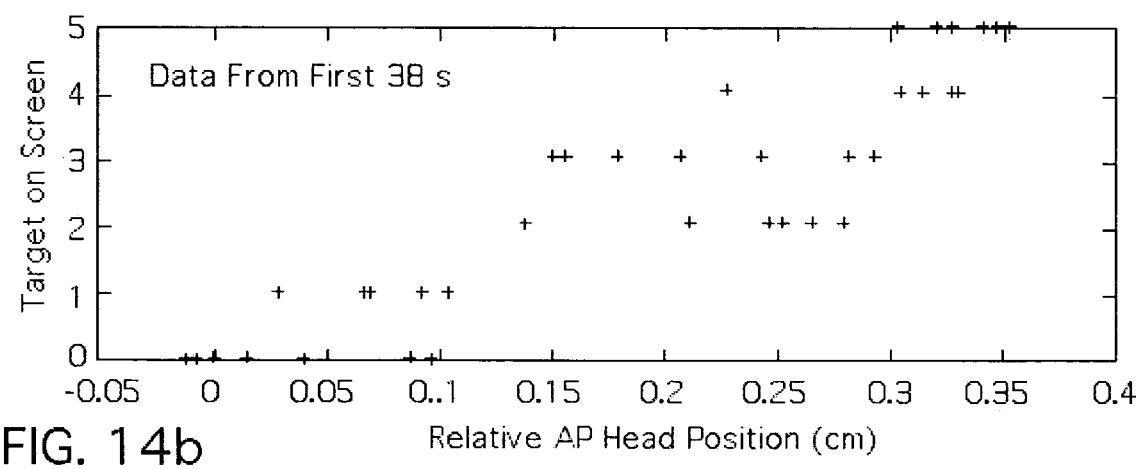

An additional comparison can be made between the head movement and the amount of work remaining at the point in time when head movement is measured. The level of remaining work is recorded at step 70 in FIG. 6A. A linear regression may then be performed between the head position and number of queued work tasks at each time increment at step 72. This correlation is calculated over time windows (intervals) that are task-specific, typically in the range of 6–25 seconds. A correlation coefficient of this linear regression may be calculated at step 74 in FIG. 6B. Referring to FIGS. 13a–b and 14a–b, the relationship between head position and tasks on the computer monitor is illustrated. Within FIG. 13a, head position is represented by curve 76, and work remaining is illustrated by curve 78. Likewise, head position is represented by curve 80 in FIG. 14a, and work remaining is represented by curve 82. As can be seen from these figures, the head will move closer to the monitor 44 as increasing number of tasks are displayed on the monitor 44, until a comfortable head position is reached. The head will remain within this comfortable position, possibly with one adjustment at points 84, 86, after which time the head will settle into a comfortable position for maintaining vigilance even as work remaining decreases, until the person 20 is satisfied that no additional tasks remain, at which point the head will return to its at-rest position. Turning to the bottom portions of FIGS. 13 and 14, showing head position as a function of work remaining, the linear relationship between the two becomes apparent, with an increasing number of targets on the screen resulting in increasing forward motion of the head towards the screen. Therefore, a good fit between head position and work remaining at each time interval, determined at step 88 in FIG. 6B, indicates that the person 20 is mentally engaged in the task, and no intervention is needed, as shown in step 90. However, if there is not a good fit between head position and work remaining, a further inquiry needs to be made to determine if the person 20 has adopted a posture of vigilance, as indicated by a high magnitude of forward positioning of the head, determined at step 94. If the head position indicates that the person 20 is being vigilant, no intervention is needed. If not, then additional stimulus may be needed to prevent boredom, or the person 20 may need to be relieved.

Figure 15:
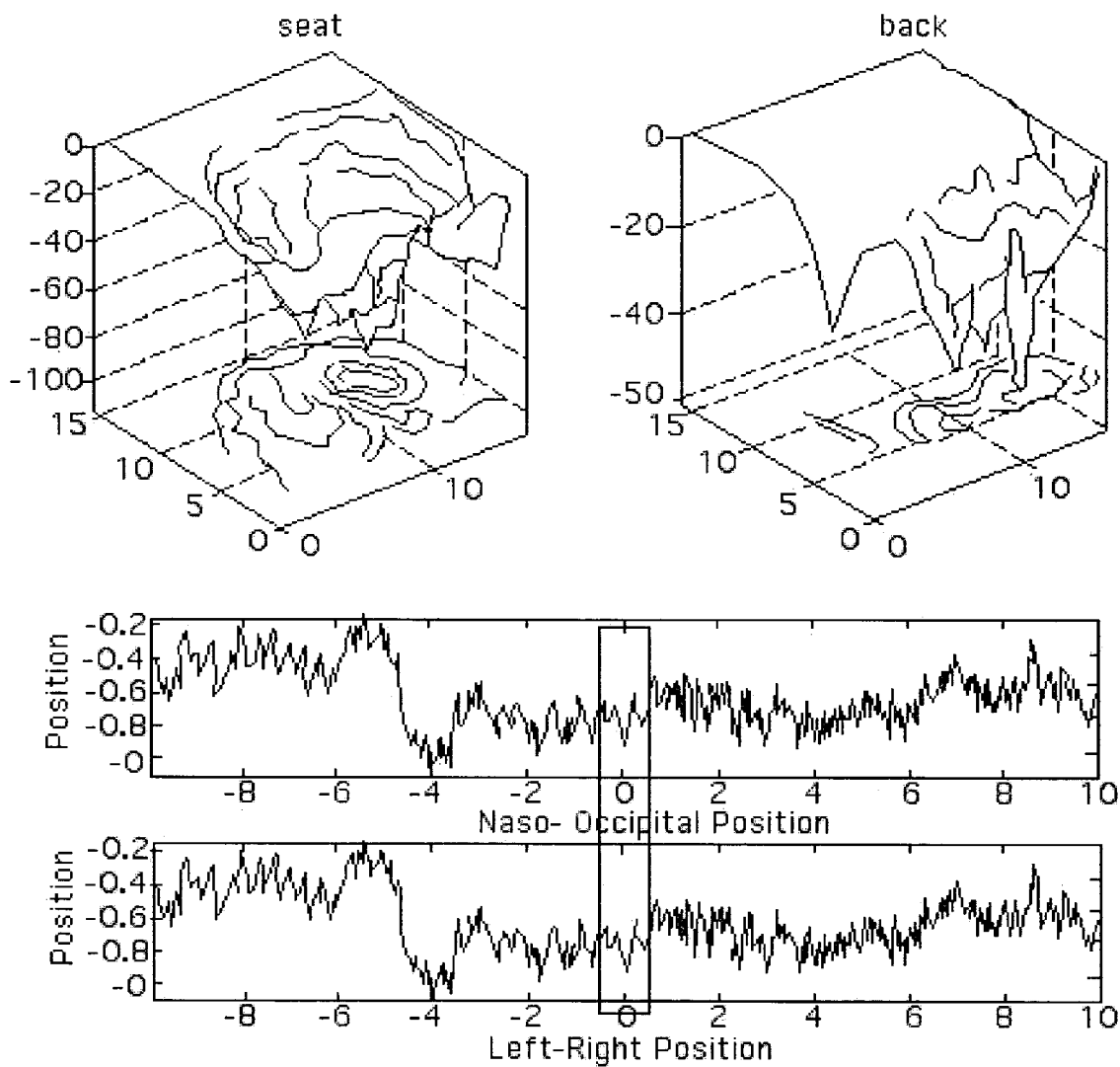
FIG. 15 is a group of graphs illustrating seat pad and back pad pressure during a high cognitive workload.
Figure 16:
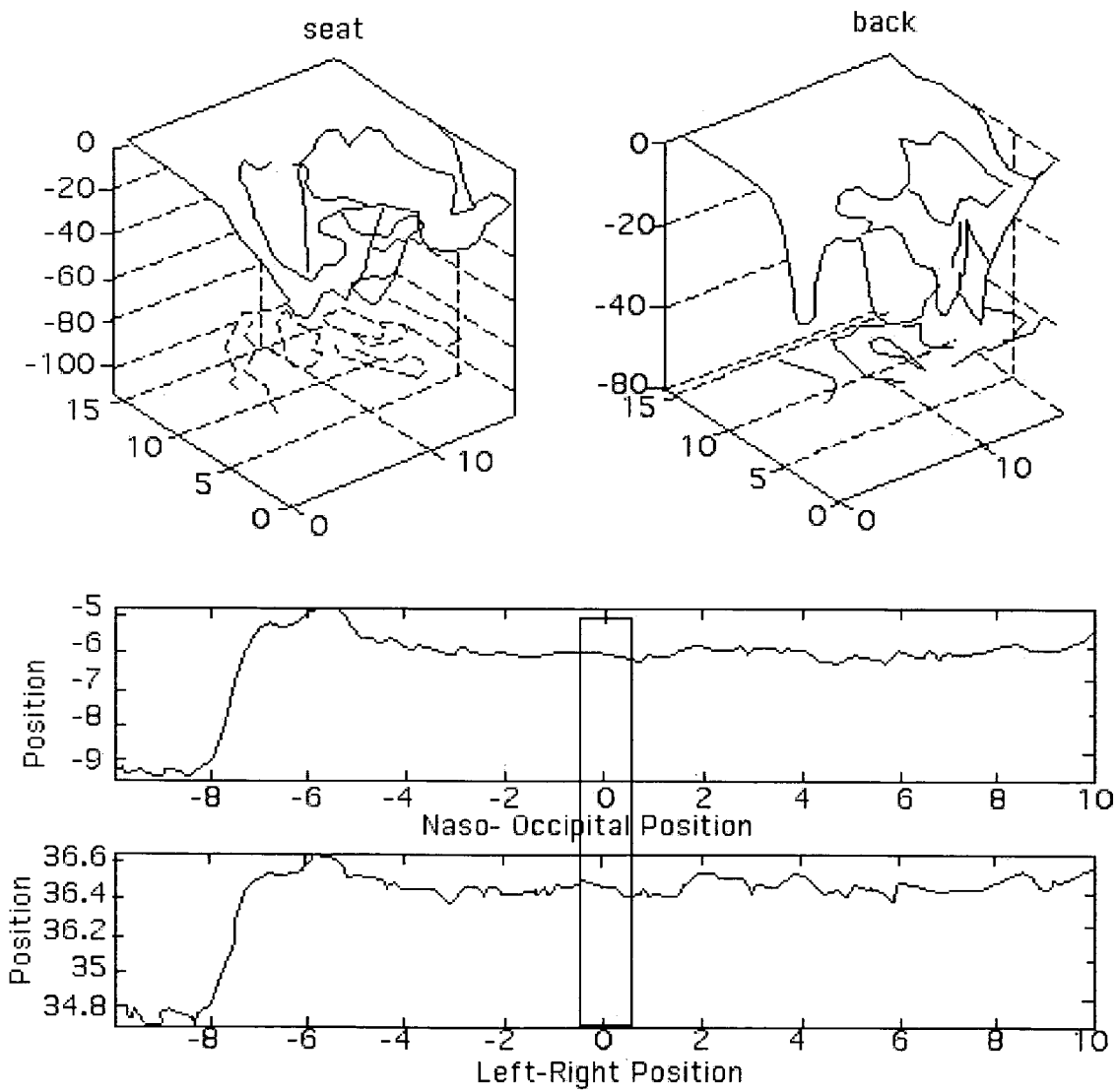
FIG. 16 is a group of graphs illustrating the seat pressure and back pad pressure exerted during periods of low cognitive workload.

FIG. 7 illustrates the method of determining the level of mental engagement using seat pressure. The expected pressure across the seat 12 and back 14 given a high cognitive workload is illustrated in FIG. 15. As this figure illustrates, there will be a relatively high pressure distributed over a smaller area of the seat and back. Additionally, the body will be braced, resulting in only small changes within the pressure distribution. Conversely, FIG. 16 illustrates the expected pressure distribution across the seat 12 and back 14 for a low cognitive workload. The more relaxed posture will result in lower pressure distributed across a wider are of the seat 12 and back 14. Furthermore, with a low cognitive workload, or high fatigue, one would expect more loosely constrained body linkages, or more frequent adjustments in posture, resulting in greater changes in the pressure distribution. Referring back to FIG. 7, the initial back and seat pressure at rest is first determined at step 94. At each time interval, the pressure at each back and seat sensor is read at step 96. The rate of change of pressure at that point in time is calculated at step 98 for each sensor. A method of calculating this rate of change is described in Burden, *Numerical Analysis*, at 146–63, expressly incorporated herein by reference. At this point, the standard deviation of the change in pressure at all sensors at the time increment in question may be calculated at step 100. It is this standard deviation that determines whether there is a likelihood that the person 20 is experiencing fatigue, which will be indicated by large changes in pressure, which will result in a large standard deviation. This comparison is made at step 102. For the above-described warship commander task, it has been found that a standard deviation of greater than 0.2 indicates that there is an 80% likelihood that the person 20 is fatigued or perceiving a reduced work load, indicating that intervention may be needed at step 104 in the form of either task modification to prevent boredom, shift of workload to other operators or relief by a new operator. Otherwise, no intervention is needed at step 106.

Figure 17A:
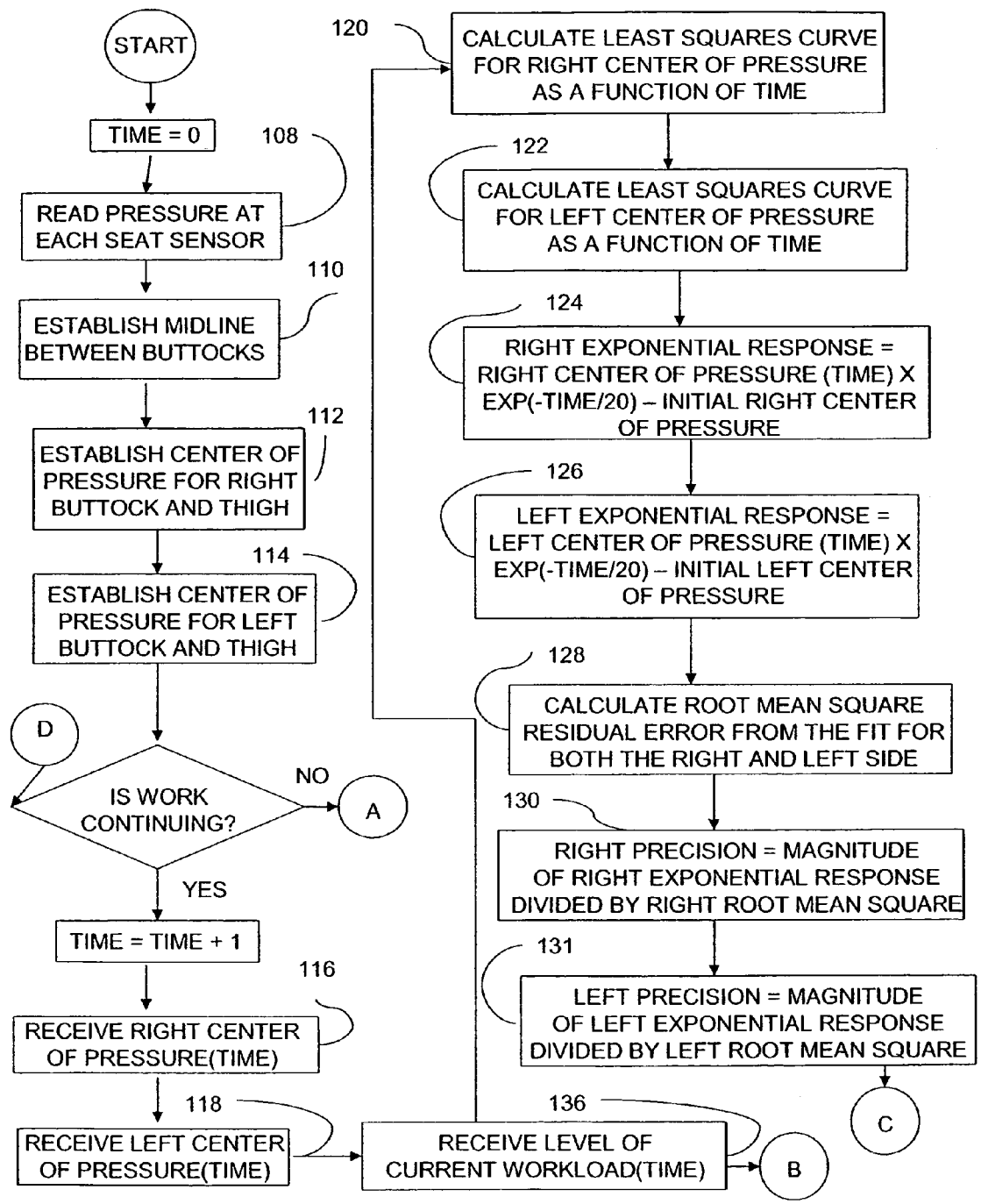
FIGS. 17A–17B are a flow chart illustrating the analysis of movement of the center of pressure applied by the right and left buttock and thigh for determining mental engagement.
Figure 17B:
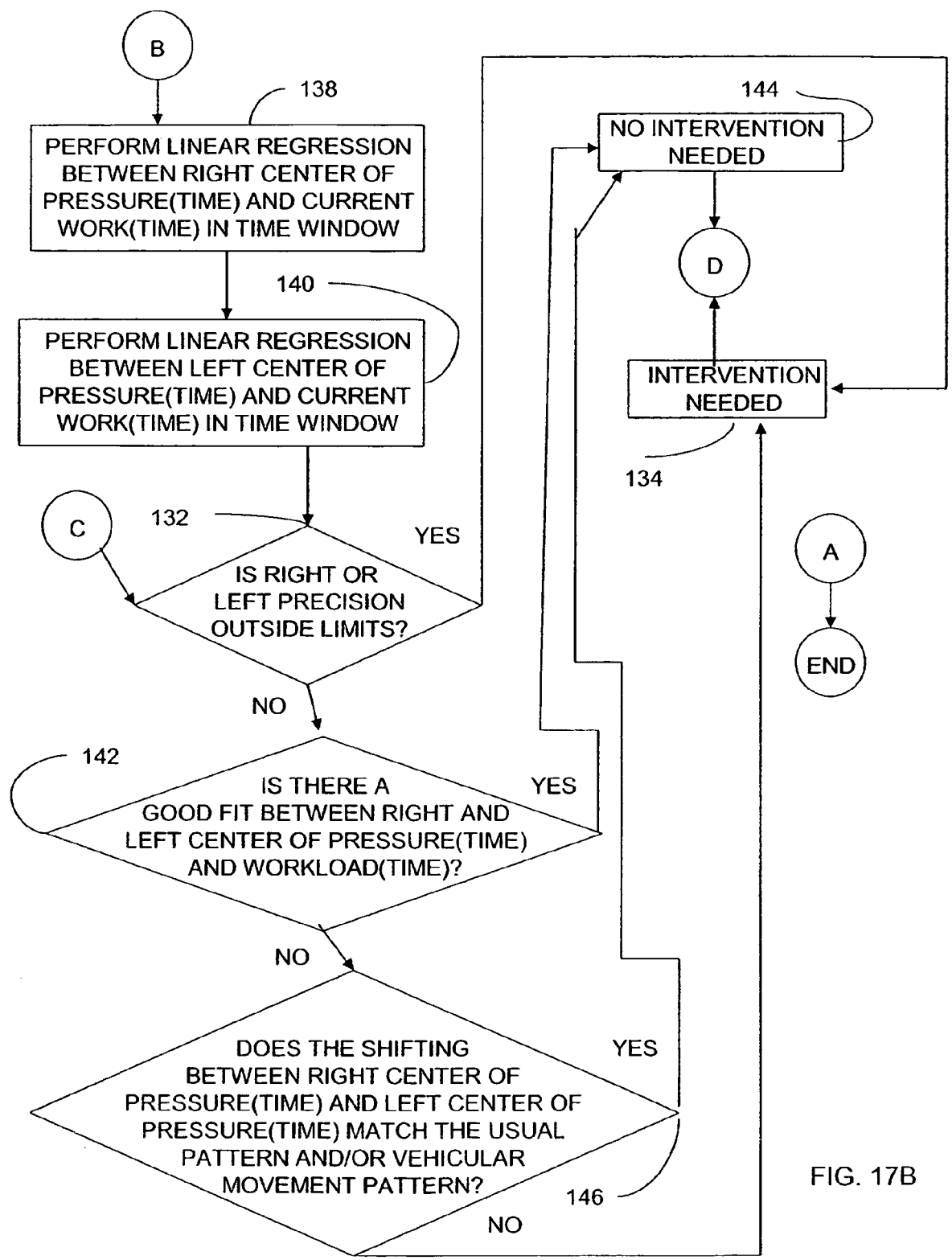

FIGS. 17A–17B explain an alternative method of using the chair 10 to monitor the posture of the person 20, and thereby monitor his level of mental engagement. FIGS. 17A–17B illustrate the use of the seat sensors to measure the movement of the center of pressure applied to the seat by the right and left buttocks and thighs, and the correlation to cognitive engagement. Initially, after reading the pressure at each sensor at step 108, the midline is established at step 110, and the starting center of pressure for the right and left buttock and thigh is read and recorded at 112,114, respectively. At each time increment, the position of the right and left center of pressure at that time is recorded at 116,118. Typically, each center of pressure will move forward, as the head moves from its rest position towards a visual stimulus. Referring briefly to FIG. 8, the head 22 will typically move towards the monitor 44 more rapidly at first, and then less rapidly, until a comfortable head position is reached for either performing the tasks or maintaining vigilance. This head movement will be matched by a movement in the center of pressure applied to the seat by the right and left buttocks. This movement of the centers of pressure can be represented by fitting the actual head movement points to a curve using least squares methodology, described in Richard L. Burden and J. Douglas Faires *Numerical Analysis, Fourth Edition*, 427–49 (1989), expressly incorporated herein by reference. This step is performed at steps 120,122 in FIG. 17A.

The movement of the right and left centers of pressure may be further analyzed by looking at an exponential response to this movement with respect to time, with exponential response=((center of pressure movement magnitude) X exp(−time/20))−(initial center of pressure). This calculation is performed at steps 124,126 within FIG. 17A. The resulting curve may be further broken down into two separate elements: the curve itself, and the error between the actual data point and the approximated curve. By calculating the amount of the error, or the root means square of the exponential response, at step 128, and then dividing the magnitude by the root means square at steps 130,131, the possible degree of error in the movement in the right and left center of pressure is determined. If this error is too high as determined at step 132 in FIG. 17B, this may be an indication that either additional stimulus or relief may be needed for the person 20, as provided at step 134 in FIG. 17B.

An additional comparison can be made between the movement of the right and left center of pressure and the number of tasks in the work queue at the point in time when these movements are measured. The level of remaining work is recorded at step 136 in FIG. 17A. A linear regression may then be performed between the right and left center of pressure and number of tasks in the work queue at each time increment at steps 138,140. A correlation coefficient of this linear regression may be calculated over a task-specific time window (typically 6–25 seconds) at step 142 in FIG. 17B. A good fit between the position of the right and left center of pressure and work remaining at each time interval indicates that the person 20 is mentally engaged in the task, and no intervention is needed, as shown in step 144. However, if there is not a good fit between the right and left center of pressure and work remaining, a further inquiry needs to be made to determine if the person 20 has adopted a posture typical of vigilance for that individual, or if the individual is reacting properly to movements of a vehicle within which the person is sitting, determined at step 146. If the position of the right and left centers of pressure indicate that the person 20 is shifting to the right and left appropriately, no intervention is needed. If not, then additional stimulus may be needed to prevent boredom, or the person 20 may need to be relieved.

Figure 4:
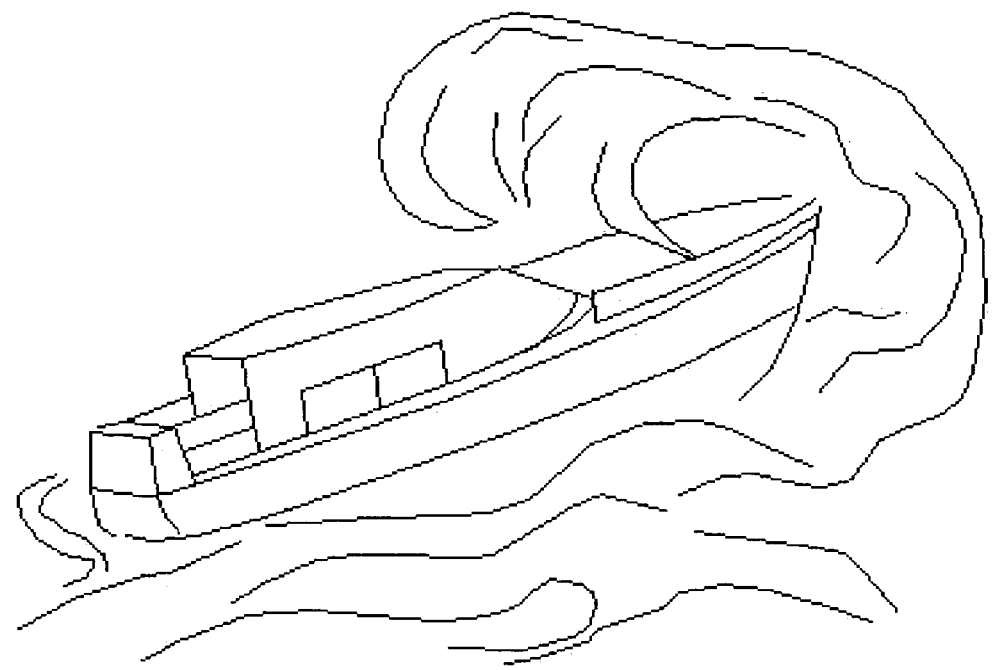
FIG. 4 is a photograph of a boat with which the present invention may be used.
Figure 5:
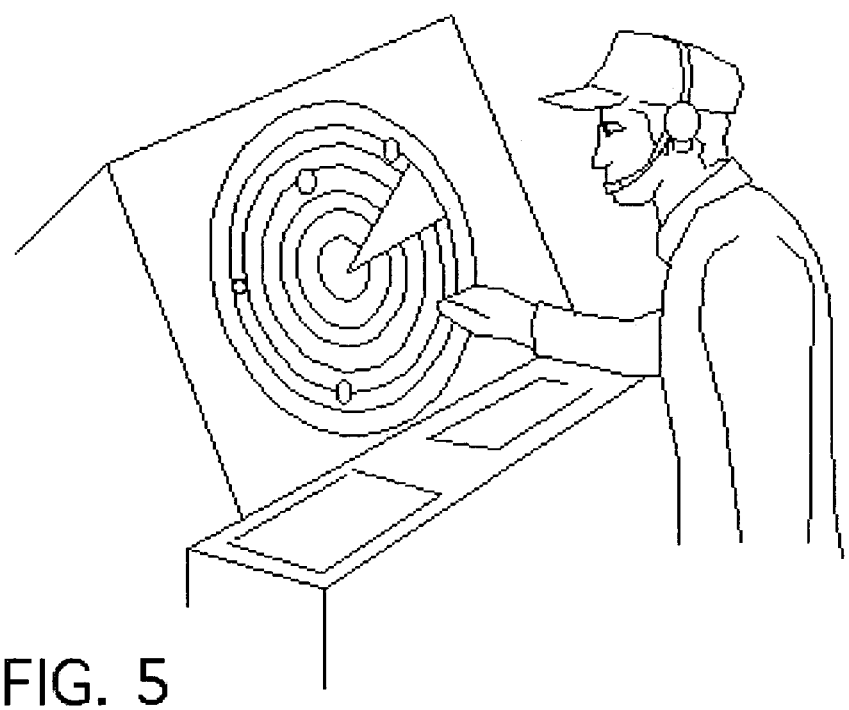
FIG. 5 is a photograph of a radar operator with whom the present invention may be used.

The correlation between head position, seat position, and cognitive engagement was tested using a "warship commander" simulation wherein the test subject was presented with up to six, or up to twenty-four, "target" airplanes on a monitor, and was required to select individual planes, inquire about their identity, warn "foe" planes away, and destroy "foe" planes that get too close. The approach developed in the Warship Commander Task was then validated in a similar Aegis command simulation task. This task differed from the Warship Commander Task in several important ways: the appearance of new targets was uncued, the targets were embedded in a more complex display and the average latency for the appearance of new targets was longer (12 seconds versus 2 seconds). The operator was required to perform three sequential types of actions, (1) hook a target, (2) select a target and (3) identify a target, with a decision process at each step whether to continue with the sequence or hook a new target. These decisions were based upon a set of priority rules. The maximum values of the correlation coefficients head position and seat center of position with the number of targets were calculated over a 12 second window, and were designated the overall engagement gauge. The quantitative performance of the subject in the task (scores based upon correct decisions) was correlated highly with the proportion of the time that the overall engagement gauge exceeded 0.5 (meaning that 50% of the center of seat position or head position changes relative to the monitor were explained by the number of targets on the screen), which supports the role of the gauge as a predictor of cognitive engagement. When at least 50% of head or seat position shifts are explained by the number of targets on the monitor, the probability of the next action occurring within 2 seconds was found to be 0.616, the probability of action within 3 seconds was 0.766, the probability of action within 4 seconds was 0.860, and the probability of action within 5 seconds was 0.946. Therefore, this device and algorithm provide a high degree of predictability of an operator's activity within the ensuing few seconds. Therefore, the present invention provides a means of monitoring changes in posture that may be indicative the degree of cognitive engagement on the part of a seated person performing cognitive work. Furthermore, changes in posture may be compared to movement of the vehicle itself. For example, if the radar operator shown in FIG. 5, on the boat in FIG. 4, is fully cognitively engaged, his changes in posture will be such that he has predicted the movements of the boat. By comparing the movement sensor in the chair to the head and/or torso sensor, or pressure pad sensor, a determination can be made as to whether the radar operator is predicting or reacting to the motions of the boat. If he is reacting to the motions of the boat, fatigue is indicated. As another example, comparing the postural changes of a helicopter pilot to the movements of the helicopter itself may indicate that the pilot has lost his sense of the correct direction of "up", and that therefore certain maneuvers of the helicopter should be prohibited. Other examples of cognitive work performed while seated for which there is a need to determine boredom and/or fatigue, and provide appropriate stimulus or relief, include airplane pilot, air traffic controller, vehicle driver, boat operator, etc. Lastly, by mounting the chair on a moveable platform, the postural assessment chair 10 may be used to test postural function in patients who are unable to stand for conventional testing.

While a specific embodiment of the invention has been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

The invention claimed is:

1. A postural assessment chat, comprising:
   a seat;
   a back;
   means for sensing postural changes of a person seated on the chair, including a pressure sensor array having a plurality of sensors disposed on at least one location selected from the group consisting of the seat and the back; and
   means for analyzing postural changes to determine a level of mental engagement from information about postural changes of the person, including:
      means for monitoring a pressure sensed at each sensor within the array;
      means for calculating a rate of change in pressure at each sensor;
      means for calculating a standard deviation of the rate of change in pressure across all sensors; and
      means for comparing the standard deviation to a predetermined threshold.

2. A postural assessment chair, comprising:
   a seat;
   a back;
   means for sensing postural changes of a person seated on the chair, including a pressure sensor array having a plurality of sensors disposed on at least one location selected from the group consisting of the seat and the back; and
   means for analyzing postural changes to determine a level of mental engagement from information about postural changes of the person, including:
      means for monitoring a pressure sensed at each sensor within the array;
      means for determining a midline separating the pressure distribution into a right and left side;
      means fir determining a center of pressure on each side of the midline; and
      means for monitoring changes in the center of pressure on each side of the midline.

3. A postural assessment chair, comprising:
   a seat;
   a back;
   means for sensing postural changes of a person seated on the chair, including a transmitter disposed on or adjacent to the chair, a reference position and orientation sensor disposed on the back, and at least one position sensor disposed on a head or a torso of the person seated on the chair; and
   means for analyzing postural changes to determine a level of mental engagement from information about postural changes of the person the means for analyzing postural changes including;
      means for monitoring changes in position of the position sensor;
      means for monitoring an amount of cognitive work remaining to be performed by the person;
      means for correlating the position of the position sensor with the work remaining to be performed;
      means for determining whether the correlation of sensor position with work remaining falls below a predetermined threshold; and
      means for comparing the sensor position with predetermined sensor movement patterns if the correlation of sensor position with work remaining falls below the predetermined threshold.

4. The chair according to claim 3, wherein the position sensor is selected from the group consisting of magnetic sensors and ultrasonic sensors.

5. A postural assessment chair, comprising:
   a seat;
   a back,
   means for sensing postural changes of a person seated on the chair, including a transmitter disposed on or adjacent to the chair, a reference position and orientation sensor disposed on the back, end at least one position sensor disposed on a head or a torso of the person seated on the chair; and
   means for analyzing postural changes to determine a level of mental engagement from information about postural changes of the person, the means for analyzing postural changes including:
      means for monitoring changes in position of the position sensor;
      means for calculating an exponential response based on changes in position with respect to time;
      means for calculating a root mean square of the exponential response; and
      means for comparing the root mean square to a magnitude of the exponential response.

6. A postural assessment chair, comprising:
   a seat;
   a back;
   means for sensing postural changes of a person seated on the chair, including a motion sensor disposed on the chair; and
   means for analyzing postural changes to determine a level of mental engagement from information about postural changes of the person wherein the means for analyzing postural changes include means for comparing postural changes of a person seated in the chair with motions detected by the motion sensor to determine whether the person is properly compensating for motions of the chair.

7. A method of determining a level of cognitive engagement of a person performing seated work, the method comprising:
   providing sensors structured to detect postural changes of the person, including providing a pressure sensor array having a plurality of sensors disposed on at least one location selected from the group consisting of the seat and the back; and comparing the postural changes to information selected from the group consisting of known thresholds, the level of cognitive work remaining, and predetermined postural patterns to determine the level of cognitive engagement of the person, including:
monitoring a pressure sensed at each sensor within the array;
calculating a rate of change in pressure at each sensor;
calculating a standard deviation of the rate of change in pressure across all sensors; and
comparing the standard deviation to a predetermined threshold.

8. A method of determining a level of cognitive engagement of a person performing seated work, the method comprising:
providing sensors structured to detect postural changes of the person, including providing a pressure sensor array having a plurality of sensors disposed on at least one location selected from the group consisting of the seat and the back; and
comparing the postural changes to information selected from the group consisting of known Thresholds, the level of cognitive work remaining, and predetermined postural patterns to determine the level of cognitive engagement of the person, including:
monitoring a pressure sensed at each sensor within the array;
determining a midline separating the pressure distribution into a right and left side;
determining a center of pressure on each side of the midline; and
monitoring changes in the center of pressure an each side of the midline.

9. A method of determining a level of cognitive engagement of a person performing seated work, the method comprising:
providing sensors structured to detect postural changes of the person, including:
providing a transmitter disposed on or adjacent to the chair;
providing a reference position and orientation sensor disposed on the back; and
providing at least one position sensor disposed on a head or a torso of the person seated on the chair; and
comparing the postural changes to information selected from the group consisting of known thresholds, the level of cognitive work remaining, and predetermined postural patterns to determine the level of cognitive engagement of the person, including;
monitoring changes in position of the position sensor;
monitoring an amount of cognitive work remaining to be performed by the person;
correlating the position of the position sensor with the work remaining to be performed;
determining whether the correlation of sensor position with work remaining falls below a predetermined threshold; and
comparing the sensor position with predetermined sensor movement patterns if the correlation of sensor position with work remaining falls below the predetermined threshold.

10. A method of determining a level of cognitive engagement of a person performing seated work, the method comprising:
providing sensors structured to detect postural changes of the person, including:
providing a transmitter disposed an or adjacent to the chair;
providing a reference position and orientation sensor disposed on the back; and
providing at least one position sensor disposed on a head or a torso of the person seated on the chair; and
comparing the postural changes to information selected from the group consisting of known thresholds, the level of cognitive work remaining, and predetermined postural patterns to determine the level of cognitive engagement of the person, including:
monitoring changes in position of the position sensor;
calculating an exponential response based on changes in position with respect to time;
calculating a root mean square of the exponential response; and
comparing the root mean square to a magnitude of the exponential response.

11. A method of determining a level of cognitive engagement of a person performing seated work, the method comprising:
providing sensor structured to detect postural changes of the person, including providing a motion sensor disposed on the chair; and
comparing the postural changes to information selected from the group consisting of known thresholds, the level of cognitive work remaining, and predetermined postural patterns to determine the level of cognitive engagement of the person wherein the step of comparing the postural changes to information selected from the group consisting of known thresholds, the current cognitive workload, number of queued tasks, the level of cognitive work remaining, and predetermined postural patterns to determine the level of cognitive engagement of the person includes comparing postural changes of a person seated in the chair with motions detected by the motion sensor to determine whether the person is properly compensating for motions of the chair.

* * * * *